US007729768B2

(12) United States Patent
White et al.

(10) Patent No.: US 7,729,768 B2
(45) Date of Patent: Jun. 1, 2010

(54) IMPLANTABLE CARDIAC MOTION POWERED PIEZOELECTRIC ENERGY SOURCE

(75) Inventors: Robert White, Stanford, CA (US); George Savage, Portola Valley, CA (US); Mark Zdeblick, Portola Valley, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 92 days.

(21) Appl. No.: 11/385,986

(22) Filed: Mar. 20, 2006

(65) Prior Publication Data
US 2006/0217776 A1 Sep. 28, 2006

Related U.S. Application Data

(60) Provisional application No. 60/665,286, filed on Mar. 25, 2005.

(51) Int. Cl.
*A61N 1/00* (2006.01)
(52) U.S. Cl. .................. 607/35; 310/319; 310/354; 310/367
(58) Field of Classification Search ............. 607/35; 310/311, 319, 330, 348, 354, 367
See application file for complete search history.

(56) References Cited

U.S. PATENT DOCUMENTS 3,456,134 A * 7/1969 Ko ........................ 607/35
3,659,615 A * 5/1972 Enger ..................... 607/35
3,943,936 A * 3/1976 Rasor et al. .............. 607/35
RE30,366 E * 8/1980 Rasor et al. .............. 607/35
4,499,394 A * 2/1985 Koal ..................... 310/330
4,661,107 A * 4/1987 Fink ..................... 623/2.34
4,798,206 A * 1/1989 Maddison et al. ......... 607/122
5,431,694 A * 7/1995 Snaper et al. ............ 607/35
5,703,474 A 12/1997 Smalser
5,801,475 A 9/1998 Kimura
6,208,065 B1 * 3/2001 Ueyama .................. 310/328
2003/0176836 A1 9/2003 Doukas et al.
2004/0021322 A1 2/2004 Ariav
2004/0158294 A1 8/2004 Thompson

OTHER PUBLICATIONS

Lu et al. "Modeling and Analysis of Micro Piezoelectric Power Generators for Micro-Electromechanical-Systems Applications," Smart Mater. Struct. (2004) 13:57-63.
Ramsay and Clark "Piezoelectric Energy Harvesting for Bio MEMS Applications," Proceedings of SPIE (2001) 4332:429-437.
White et al. "Design and Modelling of A Vibration-Powered Micro-Generator," Measurement & Control (2001) 34:267-271.
Platt et al. "On Low-Frequency Electric Power Generation with PZT Ceramics," IEEE/ASME Transactions on Mechatronics (2005) 10(2):240-252.

* cited by examiner

*Primary Examiner*—Mark W Bockelman
(74) *Attorney, Agent, or Firm*—Bret E. Field; Bozicevic Field & Francis LLP.

(57) ABSTRACT

Implantable cardiac motion powered piezoelectric energy sources are provided. An aspects of embodiments of the subject implantable energy sources is that they include a piezoelectric transducer that converts cardiac mechanical energy to electrical energy. The subject energy sources find use in a variety of applications, including providing power to a wide range of implantable devices.

22 Claims, 3 Drawing Sheets

IMPLANTABLE CARDIAC MOTION POWERED PIEZOELECTRIC ENERGY SOURCE

CROSS-REFERENCE TO RELATED APPLICATION

Pursuant to 35 U.S.C. §119 (e), this application claims priority to the filing date of: U.S. Provisional Patent Application Ser. No. 60/665,286 filed Mar. 25, 2005; the disclosure of which is herein incorporated by reference.

BACKGROUND

A variety of different kinds of implantable medical devices (IMD) are known in the art, which devices may have one or more different functions, including, but not limited to: monitoring of physiological parameters; delivery of pharmacological agents; and delivery of electrical stimuli.

Many IMDs require a source of power to function. Conventional IMDs may receive power from a dedicated battery. While battery-based power sources have proven useful in the medical arts, there are drawbacks to such power sources. For instance, a fully implanted system is not easily subject to re-supply should the battery power be expended. When a medical device is powered through an externally protruding wire, there is the risk that infection may follow this wire to vulnerable areas of the body. Additionally, when implanted, the possibility of corrosion or loss of liquid battery components or exposure of solid components to the body are likely to have physiologically disadvantages results.

It would be an important advancement in the art if a robust implantable motion powered energy source could be developed.

SUMMARY

Implantable cardiac motion powered piezoelectric energy sources are provided. Aspects of the subject implantable energy sources include the presence of a piezoelectric transducer that converts cardiac mechanical energy to electrical energy. The subject energy sources find use in a variety of applications, including providing power to a wide range of implantable devices.

DESCRIPTION OF THE SPECIFIC EMBODIMENTS

Figure 1A:
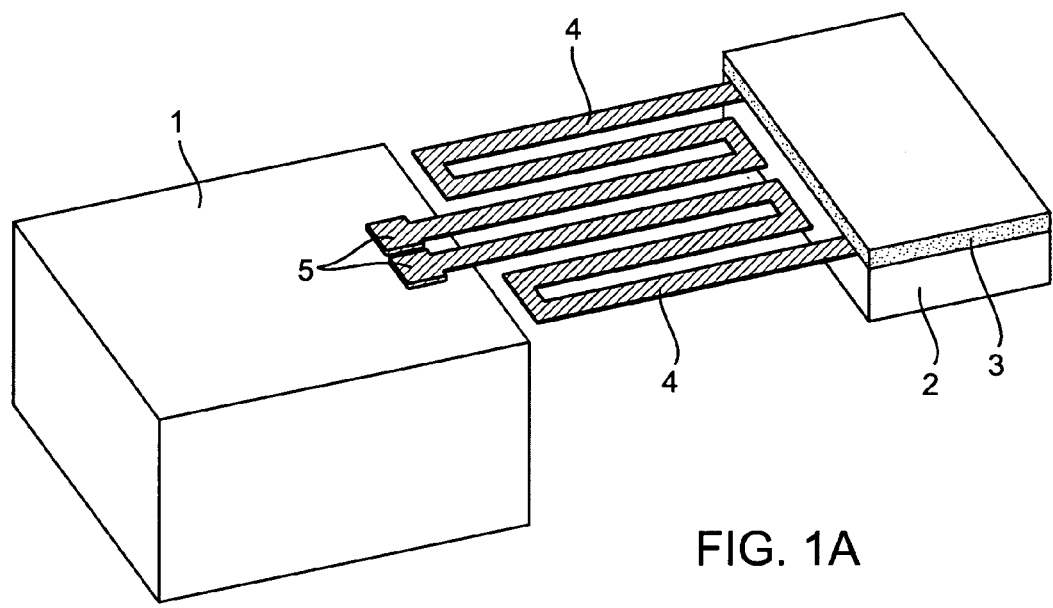
FIGS. 1A to 1C provide various views of an implantable cardiac motion powered piezoelectric energy source according to a first embodiment of the invention.

Implantable cardiac motion powered piezoelectric energy sources are provided. Aspects of the subject implantable energy sources include the presence of a piezoelectric transducer that converts cardiac mechanical energy to electrical energy. The subject energy sources find use in a variety of applications, including providing power to a wide range of implantable devices.

Before the present invention is described in greater detail, it is to be understood that this invention is not limited to particular embodiments described, and the invention as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention provides implantable cardiac motion powered piezoelectric energy sources, as well as systems and kits thereof and methods for their preparation and use. In further describing the subject invention, the subject energy sources and their preparation are described first in greater detail, followed by a review of applications in which they find use. Also provided is a review of the kits and systems of the subject invention.

Implantable Cardiac Motion Powered Piezoelectric Energy Sources

As summarized above, the present invention provides implantable cardiac motion powered piezoelectric energy sources. The implantable cardiac motion energy sources of the invention are energy sources that may be positioned at a cardiac site and function without significant, if any, deterioration for extended periods of time. As such, once implanted, the energy sources do not deteriorate in terms of function for a period of at least about 2 or more days, such as at least about 1 week, at least about 4 weeks, at least about 6 months, at least about 1 year or longer, e.g., at least about 5 years or longer.

As summarized above, the implantable motion powered energy sources may be characterized as cardiac. The phrase "cardiac" as employed herein denotes that the energy sources are configured (e.g., shaped, dimensioned etc.) so that they can be positioned at a cardiac location, e.g., in a heart chamber, such as an atrium or ventricle, including the left ventricle, at an epicardial site, on or in a ventricular wall, etc., of a living organism, such as a mammal, e.g., a human. In certain embodiments, the energy sources have a longest outer dimension, e.g., length, which does not exceed about 5 mm, such as a length that does not exceed about 3 mm, including a length that does not exceed about 2 mm. In certain embodiments, the volume of (or space occupied by) the energy source does not exceed about 50 mm$^3$, and in certain embodiments does not exceed about 10 mm$^3$.

As summarized above, the cardiac motion powered energy sources of the invention are piezoelectric energy sources. By piezoelectric energy source is meant that the energy source includes a piezoelectric transducer that converts cardiac mechanical energy into electrical energy. As such, the energy source includes a piezoelectric element made of a piezoelectric material. Any convenient piezoelectric material (PEM) may be used, where a variety of different piezoelectric materials are known in the art, including but not limited to: piezoelectric crystals, piezoelectric ceramics, piezoelectric polymers or composites thereof. Numerous different PEMs are currently known. Among these are crystalline substances whose unit crystal structure lacks a center of symmetry. Examples, without limitation of such substances are tourmaline, potassium sodium nitrate, Rochelle salt and quartz. Polycrystalline substances which have been placed in a polarized state can also exhibit a piezoelectric effect and are called piezoelectric ceramics. Examples of piezoelectric ceramics include, without limitation, barium titanate (BaTiO$_3$) and lead zirconium titanate (PZT, PbZrTiO$_3$). In addition to piezoelectric crystals and ceramics, a number of polymeric materials are known to exhibit a piezoelectric effect. Most notable among these is polyvinylidene fluoride (PVDF), as well as co-polymers of PVDF, such as poly(PVDF-co-trifluoroethylene) and poly(PVDF-co-tetrafluoroethylene), polyparaxylene, poly(bischloromethyloxetane), aromatic polyamides, polysulfone, polyvinyl fluoride, polysilicon, synthetic polypeptides and cyanoethylcellulose. In certain embodiments, the employed piezoresistor material is platinum, though other materials such as polysilicon or single-crystal silicon may be used.

A feature of the subject cardiac motion energy sources is that they are matched to the dynamics of movement, e.g., contractile motion, of a heart, particularly in terms of frequency and magnitude of acceleration. The dynamics to which the energy source is matched may vary, but in certain embodiments, the heart motion dynamics include a frequency of mechanical motion ranging from about 50 to 1000 Hz, such as from about 100 to about 300 Hz, and an amplitude of acceleration ranging from about 0.5 to about 10 G, such as from about 0.5 to about 5 G, e.g., from about 1 to 2 G.

By "matched" is meant that at least the natural (i.e., resonant) frequency of the piezoelectric transducer is substantially the same as the frequency of the of the heart motion that is providing the mechanical energy to the transducer, such that any variation in these frequencies has a magnitude of not more than about 500 Hz, such as not more than about 300 Hz. Accordingly, in certain embodiments, the piezoelectric transducer has a natural frequency that ranges from about 50 to 1000 Hz, such as from 50 to about 500 Hz, including from about 100 to about 300 Hz.

The output of the subject transducer is sufficient to provide power to an implantable medical device, as reviewed below. In certain embodiments, the output is at least about 5 µW or more, such as at least about 10 µW including at least about 50 µW or more, where in certain embodiments the output may range from about 0.5 to about 50 µW, such as from about 1 to about 10 µW.

In certain embodiments, the cardiac motion powered energy source has a "weight-on-a-spring" configuration, where the piezoelectric transducer includes a beam element that includes the piezoelectric material, a proof mass at one end of the beam element and a clamp at the other end of the beam element.

The beam element has a spring constant that is chosen in conjunction with the proof mass to provide for the desired resonant frequency. The beam element may be fabricated from a number of different materials, where certain materials of interest include, but are not limited to: silicon. The beam element generally includes at least one planar surface having a piezoelectric material disposed therein, e.g., in the form of a piezoelectric layer. In certain embodiments, the beam may include two opposing planar surfaces having piezoelectric material layers disposed thereon. In certain embodiments where the length of the beam element exceeds about 5 mm, and typically about 3 mm, the beam may have a folded configuration, as reviewed in greater detail below. The transducer may have a single beam or multiple beams, e.g., 2 or more, 3 or more, 4 or more etc., depending on the particular configuration.

The proof mass at one end of the beam may have any convenient configuration, where the proof mass may be square shaped, spherical shaped, etc. The proof mass may be fabricated from any convenient material, including but not limited to silicon, and the like, where in certain embodiments the proof mass may be a composite that includes a heavy metal, e.g., platinum, iridium, etc.

At the other end of the beam is a clamp element, which clamp element serves to stably associate the transducer to a cardiac location, e.g., via additional elements present on a housing, such that heart motion is communicated to the transducer as mechanical energy. The clamp element may have any convenient configuration, where certain configurations are reviewed in greater detail below.

Figure 1B:
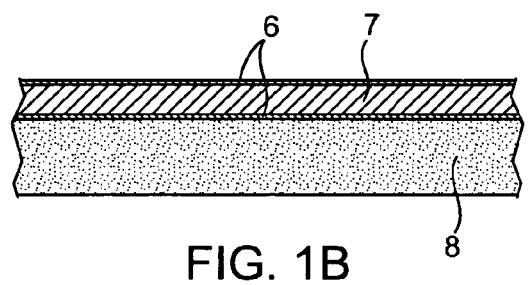
Figure 1C:
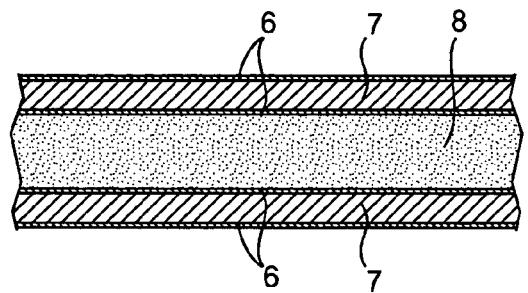
Figure 2:
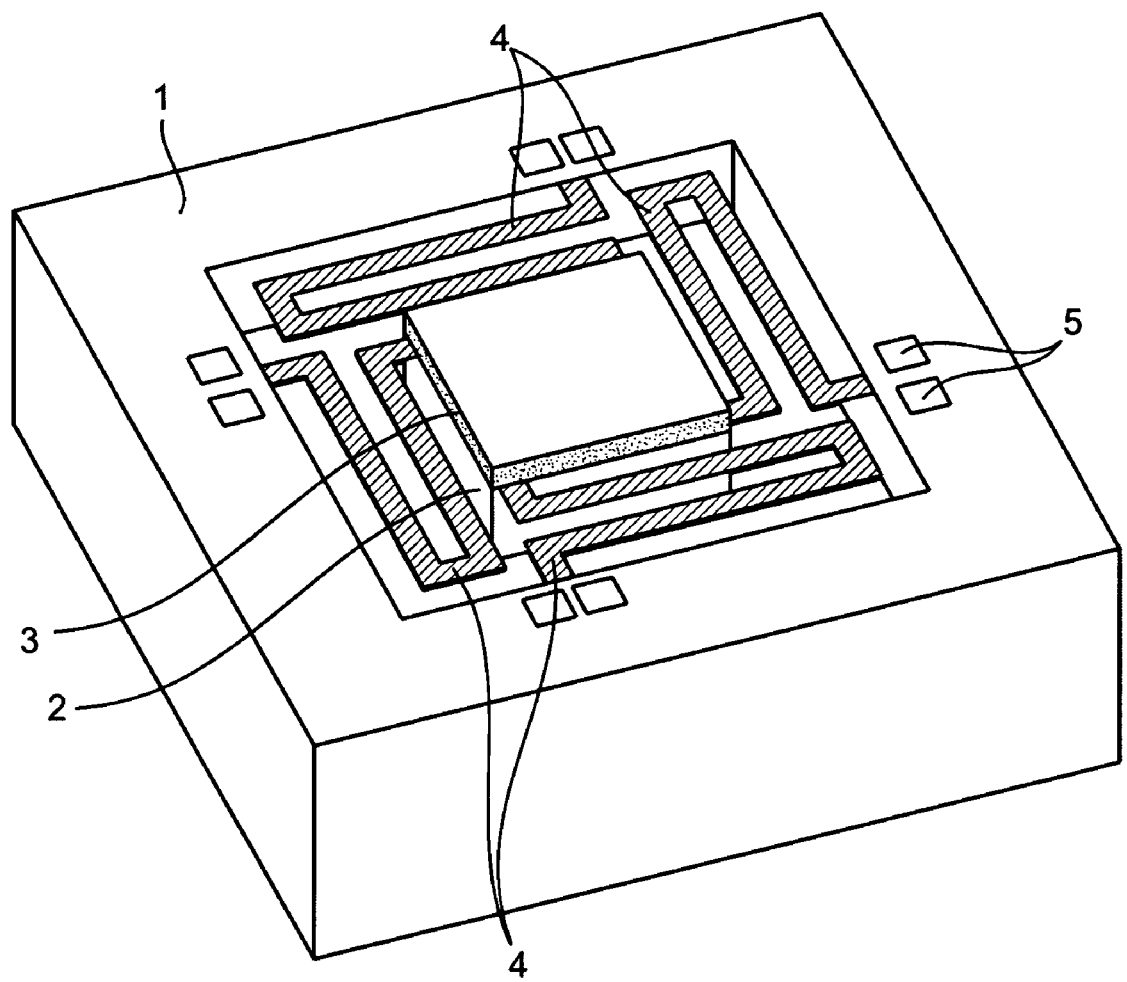
FIG. 2 provides a view of an implantable cardiac motion powered piezoelectric energy source according to a second embodiment of the invention.
Figure 3:
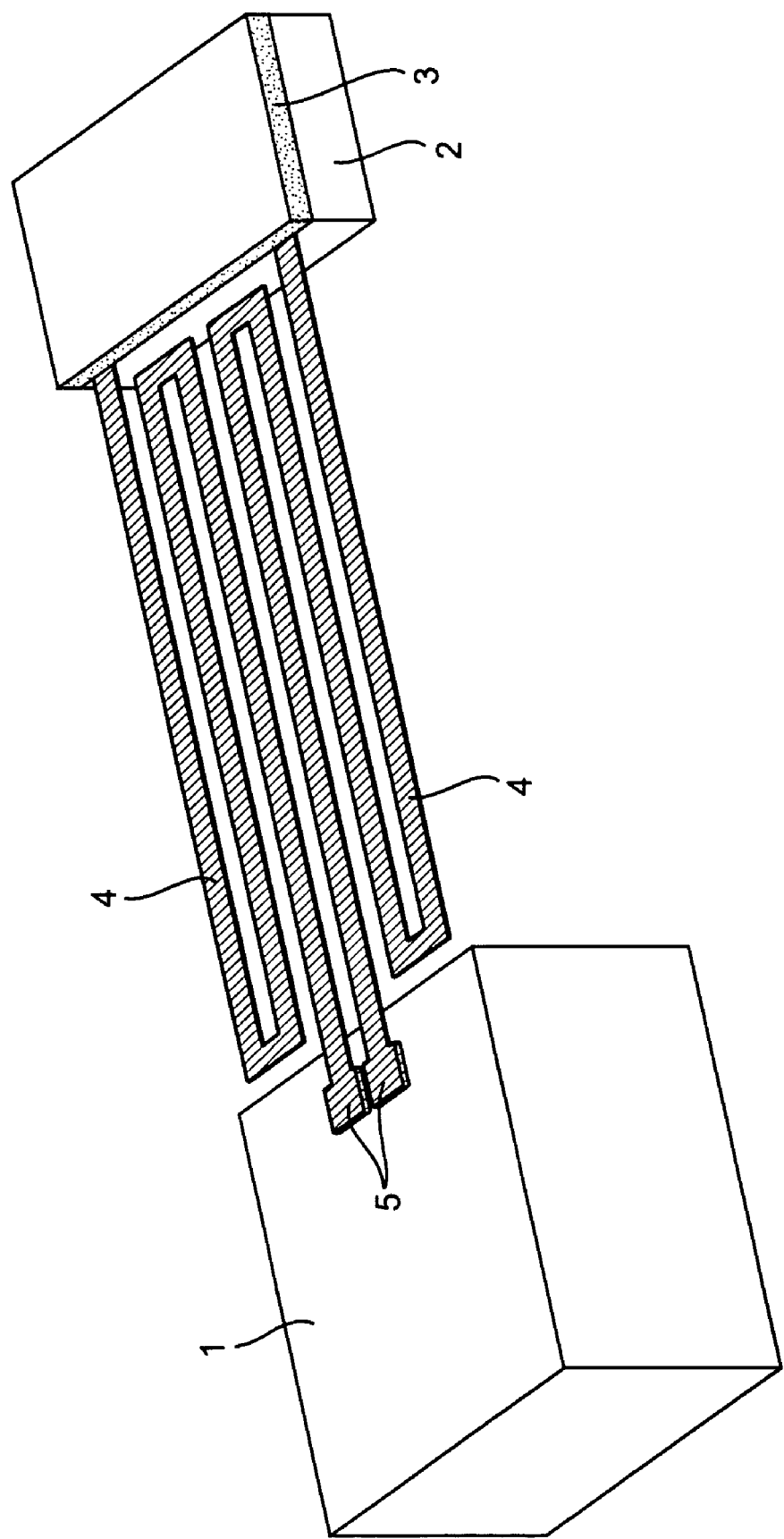
FIG. 3 provides a view of an implantable cardiac motion powered piezoelectric energy source according to a third embodiment of the invention.

Certain embodiments of the cardiac motion powered piezoelectric energy sources or generators of the present invention include those depicted in FIGS. 1 to 3.

FIG. 1A shows an embodiment of the piezoelectric transducer that includes a proof mass 2 at the end of folded beam springs 4 attached to a clamp structure 1. The clamp structure is firmly attached to an encapsulating structure (e.g., in the form of a sealed housing) not shown, which is in turn mounted on the wall of the heart. When the heart beats the proof mass is set into oscillation on the end of the beams 4. The clamp 1, proof mass 2, and core of the spring beam 4 are micro-machined from silicon using well-known MEMS technologies. Typical dimensions of the structure include a length of from about 2 to 5 mm, a width of from about 0.5 to 2 mm and thickness different for the various device sections ranging from about 2 mm down to 10 .mu.m. A silicon beam core 8 has mounted on it either in single-sided fashion (as depicted in FIG. 1B) or in double-sided fashion (as depicted in FIG. 1C) a piezoelectric film 7 sandwiched between two thin conductors 6 which collect the electric charges on the surfaces of the piezoelectric film 7 and deliver them to the electrodes 5. Details of the interconnection from the beam conductors to the electrodes are not shown. The spring structures are folded to increase their length and to lower their spring constant, and lower the resonant frequency of the proof mass oscillations. A layer of a heavy metal such as platinum or iridium on the proof mass lowers the frequency of the oscillations. The embodiment depicted in FIG. 1 has resonant frequencies in the range of 100 to 500 Hz. Although not shown, the transducer is sealed in a hermetic case to prevent fluids from surrounding the oscillating mass and damping its motion.

A second embodiment of the device is shown in FIG. 2. In the device shown in FIG. 2, the proof mass 2 is centered in its supporting clamp structure 1 and mounted on folded beams 4 at the corners. This structure has the advantage of greater stability against motions in directions other than perpendicular to the major planes of the structure. The numbered components have the same meaning as in FIG. 1.

FIG. 3 is a variation on the structure of FIG. 1 showing that such a structure can be elongated along its principal axis. Such elongation further lowers the spring constant of the beams and lowers the frequency of the resonant oscillations. The power generated increases with the surface area of the piezoelectric beams, so elongating the structure also has the beneficial effect of increasing the device power output.

For all these structures the mounting and encapsulation may include mechanical stops which prevent excess motion, perhaps damaging the springs, in the event of exposure to a high G acceleration, for instance in an automobile accident.

In addition to the piezoelectric transducer, the energy sources of the subject invention typically include a storage element for storing electrical energy that is the output of the transducer. In certain embodiments, the energy storage element may be a storage capacitor. In some embodiments of the invention, the energy storage element may include additional components to pump energy into the storage capacitor, thereby incrementally increasing the energy stored by energy storage device.

As indicated above, the piezoelectric transducer is typically sealed in a housing. The housing may have any convenient configuration, and may be present in a lead or other structure depending on the intended use of the generator and system in which it is employed. Also as indicated above, the housing may include mechanical stops that limit the range of motion of the proof mass.

Methods of Fabrication

The subject cardiac motion powered energy sources or generators may be fabricated using any convenient protocol. In certain embodiments, the fabrication protocol that is employed is a microfabrication protocol, such as a planar processing protocol, e.g., as is employed in MEMS fabrication protocols. As is known in the art, Micro-Electro-Mechanical Systems (MEMS) is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices. Such fabrication protocols are readily developed using the figures and related discussion provided herein.

Systems

Also provided are systems that include the subject energy sources. The systems include the subject energy sources and at least one implantable medical device that is powered by the energy source. The implantable medical device may have a number of different components or elements, where such elements may include, but are not limited to: sensors (e.g., cardiac wall movement sensors, such as wall movement timing sensors), cardiac stimulation elements and related structures, e.g., pacing leads with electrodes disposed thereon; processing elements, e.g., for controlling timing of cardiac stimulation, e.g., in response to a signal from one or more sensors; telemetric transmitters, e.g., for telemetrically exchanging information between the implantable medical device and a location outside the body; drug delivery elements, etc. As such, the subject power sources or generators may be operably coupled, e.g., in electrical communication with, and thereby power a number of different types of implantable medical devices, where such devices include, but are not limited to: physiological parameter sensing devices; drug delivery devices, electrical (e.g., cardiac) stimulation devices, etc.

Numerous different implantable medical devices are known in the art, where certain medical devices that may be readily adapted to be powered by appropriate embodiments of the subject energy sources include, but are not limited to, those described in: U.S. Pat. Nos.: 6,804,555; 6,795,732; 6,760,623; 6,760,619; 6,754,530; 6,748,268; 6,735,472; 6,704,598; 6,643,546; 6,591,143; 6,584,362; 6,560,489; 6,540,699; 6,421,565; 6,415,183; 6,339,724; 6,238,420; 6,223,082; 6,223,079; 6,163,723; 6,144,866; 6,078,835; 6,070,100; 6,009,349; 5,628,777; 5,549,650; 5,496,361; 5,480,412; 5,454,838; 5,423,883; 5,247,945; 5,174,288; 4,917,115; 4,858,611; 4,848,352 and 4,600,017; the disclosures of which are herein incorporated by reference.

In certain embodiments, the energy source is present in a system that includes an implantable medical device electrically coupled to ((i.e. the device is in electrical or conductive communication with) the energy source via a multiplex catheter, e.g., as described in Published PCT Application No. WO 2004/052182 and U.S. patent application Ser. No. 10/734,490, the disclosure of which is herein incorporated by reference. In certain embodiments, the energy source of the present invention is coupled to a system as described in currently pending patent applications U.S. patent application Ser. No. 10/764,429 entitled "Method and Apparatus for Enhancing Cardiac Pacing", U.S. patent application Ser. No. 10/764,127 entitled "Methods and Systems for Measuring Cardiac Parameters", U.S. patent application Ser. No. 10/764,125 entitled "Method and System for Remote Hemodynamic Monitoring" all filed Jan. 23, 2004, and U.S. patent application Ser. No. 10/734,490 entitled "Method and System for Monitoring and Treating Hemodynamic Parameters" filed Dec. 11, 2003; One Wire Medical Monitoring and Treating Devices, U.S. Patent Application No. 60/607,280 filed Sep. 2, 2004, and Implantable Doppler Tomography System U.S. Patent Application No. 60/617,618 filed Oct. 8, 2004. These applications are herein incorporated into the present application by reference in their entirety.

In some embodiments of the invention, the system may include onboard logic circuitry or a processor. Circuits such as non-clocked logic circuits may be configured to operate with low supply voltages such as the voltages generated by a motion-powered energy source of the invention. In this way, a device may be self-powered. A motion-powered energy source may support a sensor that not only detects or measures a sensed condition, but also processes information as a function of the detection or measurement. A motion-powered energy source may support a therapeutic element that not only delivers therapy, but performs computations pertaining to the mode of therapy delivered.

Methods

Also provided are methods of using the subject energy sources and systems that include the same. In general, methods of powering an implantable medical device are provided. In practicing the subject methods, an energy source or generator of the present invention is positioned or implanted at a cardiac location, e.g., as described above. Following implantation, cardiac motion is converted by the transducer to electrical energy, which is in turn stored and/or used to power an implantable medical device. For example, where the energy source will power a cardiac sensor and/or cardiac electrical stimulator, following implantation, the power source may provide power to one or more sensor components to sense one or more cardiac parameters, and or power a cardiac stimulation device to perform a particular therapeutic task, e.g., pacing or cardiac resynchronization therapy; or power a drug delivery device, etc.

The subject implantable cardiac motion piezoelectric energy sources or generators may be used to power a variety of different types of implantable medical devices, as described above, and therefore find use in a variety of different medical applications, including diagnostic applications and therapeutic applications, e.g., where drug delivery and/or electrical stimulation is employed as a therapeutic agent. The subject power sources may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the subjects or patients will be humans.

In certain embodiments of interest, the subject power sources or generators are employed to power cardiac sensors and or cardiac therapeutic devices, e.g., electrical stimulation devices, such as pacers. Certain applications of interest in these embodiments include, but are not limited to cardiac resynchronization intervention, arrhythmia management, ischemia detection, coronary artery disease management, heart failure management, among other types of applications. These applications are now reviewed in greater detail below.

Cardiac resynchronization therapy is an important new medical intervention for patients suffering from congestive heart failure. In congestive heart failure, symptoms develop due to the inability of the heart to function sufficiently well as a mechanical pump to supply the body's physiologic needs. Congestive heart failure is characterized by gradual decline in cardiac function punctuated by severe exacerbations leading eventually to death. It is estimated that over five million patients in the United States suffer from this malady.

The aim of resynchronization pacing is to induce the interventricular septum and the left ventricular free wall to contract at approximately the same time. Resynchronization therapy seeks to provide a contraction time sequence which will most effectively produce maximal cardiac output with minimal total energy expenditure by the heart.

The optimal timing is calculated by reference to hemodynamic parameters such as dp/dt, the first derivative of the pressure waveform in the left ventricle. The dp/dt parameter is a well-documented proxy for left ventricular contractility. In this manner, synchrony is assessed between various parameters such as a dp/dt, the first derivative of the pressure curve correlated to maximal relative velocity during systole towards the center of the ventricle. Also provided is the actual maximum position of displacement on a net basis of the monitored wall segments towards the center. The present inventive implantable pressure sensors allow real time analysis of the efficacy of a particular resynchronization electrode placement or pacing timing, as well as providing immediate, real time hemodynamic parameters.

The subject devices may be employed to power a cardiac sensor (such as a cardiac wall motion sensor) that is part of a CRT system, and/or a stimulation component of an implantable device, e.g., to perform CRT, as described above. For example, the subject energy sources may be coupled to and thereby power one or more sensors for measuring a cardiac parameter for use in CRT, e.g., heart wall motion and timing thereof, as well as other parameters thereof. The sensor/power generator may be combined into a single element, which element may be in communication with a cardiac stimulation component of a CRT system, e.g., via wires or wireless means. The subject generator may also power the cardiac stimulation component, as desired.

Kits

As summarized above, also provided are kits and systems for use in practicing the subject methods. The kits and systems at least include the subject energy sources and/or systems that include the same, as described above. The kits and systems may also include a number of optional components that find use with the subject energy sources, including but not limited to, implantation devices, data analysis elements, processing algorithms recorded on suitable media, etc.

In certain embodiments of the subject kits, the kits will further include instructions for using the subject devices or elements for obtaining the same (e.g., a website URL directing the user to a webpage which provides the instructions), where these instructions are typically printed on a substrate, which substrate may be one or more of: a package insert, the packaging, reagent containers and the like. In the subject kits, the one or more components are present in the same or different containers, as may be convenient or desirable.

It is evident from the above discussion and results that the subject invention provides for numerous advantages. Aspects of the invention include an implantable medical device powered by a motion-powered energy source of the subject invention that need not rely on a dedicated battery. In addition, embodiments of the invention may result in a saving of space. The implantable medical device need not have a bulky battery, allowing the element to be more miniaturized and more versatile. The motion-powered energy source is also small and saves space. Furthermore, a motion-powered energy source does not run down like a battery, but may generate power for an indefinite period of time. The motion-powered energy source may be placed proximate to an organ that moves, such as the gastrointestinal system or diaphragm, and may generate power from the motion of the organ. When placed proximate to a heart so that the motion-powered energy source moves with each beat of a heart, the motion-powered energy source will continue to generate power as long as the heart continues to beat. As such, embodiments of the subject invention represent a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An implantable cardiac motion powered energy source comprising:
   (a) a piezoelectric transducer that converts cardiac mechanical motion into electrical energy, wherein said piezoelectric transducer includes:
      (i) a piezoelectric beam element, wherein said piezoelectric beam element is folded into a structure that comprises two beam parallel lengths that define an intervening void space;
      (ii) a proof mass at one end of said beam element; and
      (iii) a clamp element at another end of said beam element; and
   (b) a storage element for storing electrical energy produced by said piezoelectric transducer.

2. The implantable cardiac motion powered energy source according to claim 1, wherein said energy source is dimensioned to be implanted at a cardiac location.

3. The implantable motion powered energy source according to claim 2, wherein said cardiac location is a heart chamber.

4. The implantable cardiac motion powered energy source according to claim 2, wherein said cardiac location is an epicardial location.

5. The implantable cardiac motion powered energy source according to claim 1, wherein said motion powered energy source has a natural frequency ranging from about 50 to about 1000 Hz.

6. The implantable cardiac motion powered energy source according to claim 5, wherein said cardiac motion powered energy source has a natural frequency ranging from about 100 to about 300 Hz.

7. The implantable cardiac motion powered energy source according to claim 1, wherein said cardiac motion powered energy source includes mechanical stops for limiting range of motion of said proof mass.

8. The implantable cardiac motion powered energy source according to claim 7, wherein said implantable medical device is a cardiac stimulation device.

9. The implantable cardiac motion powered energy source according to claim 1, wherein said cardiac motion powered energy source is in electrical communication with an implantable medical device.

10. A system comprising:
    (a) an implantable medical device; and
    (b) an implantable cardiac motion powered energy source according to claim 1 in electrical communication with said implantable medical device.

11. The system according to claim 10, wherein said implantable medical device is a cardiac stimulation device.

12. A method comprising:
    producing electrical energy from cardiac mechanical energy with an implantable cardiac motion powered energy source according to claim 1 that is positioned at a cardiac location; and
    powering an implantable medical device with energy produced by said implantable cardiac motion powered energy source.

13. The method according to claim 12, wherein said method further comprises storing electrical energy produced by said source in an energy storage element.

14. A kit comprising:
    an implantable cardiac motion powered energy source according to claim 1.

15. The kit according to claim 14, wherein said kit further comprises an implantable medical device.

16. The kit according to claim 15, wherein said implantable medical device is a cardiac stimulation device.

17. The kit according to claim 16, wherein said cardiac stimulation device is a cardiac resynchronization therapy device.

18. The implantable cardiac motion powered energy source according to claim 1, further comprising a housing, wherein said piezoelectric transducer and storage element are sealed in the housing.

19. The implantable cardiac motion powered energy source according to claim 1, wherein said cardiac motion powered energy source has a natural frequency that is matched to cardiac motion.

20. The implantable cardiac motion powered energy source according to claim 1, wherein the length of the piezoelectric beam element is 5 mm or more.

21. The implantable cardiac motion powered energy source according to claim 1, wherein the piezoelectric transducer produces electrical energy of 5 µW or more.

22. The implantable cardiac motion powered energy source according to claim 1, wherein the piezoelectric transducer produces electrical energy of 10 µW or more.

* * * * *